(12) United States Patent
Mastradonato et al.

(10) Patent No.: US 6,828,308 B2
(45) Date of Patent: Dec. 7, 2004

(54) COMPOSITIONS AND METHODS FOR THE TREATMENT OR PREVENTION OF INFLAMMATION

(75) Inventors: Marco Mastradonato, Milan (IT); Gianluca Braguti, Lecco (IT)

(73) Assignee: Sinclair Pharmaceuticals, Ltd., Godalming (GB)

( * ) Notice: Subject to any disclaimer, the term of this patent is extended or adjusted under 35 U.S.C. 154(b) by 129 days.

(21) Appl. No.: 10/080,736

(22) Filed: Feb. 22, 2002

(65) Prior Publication Data

US 2002/0183278 A1 Dec. 5, 2002

Related U.S. Application Data

(63) Continuation-in-part of application No. 10/080,624, filed on Feb. 21, 2002, now abandoned, which is a continuation-in-part of application No. PCT/EP01/08303, filed on Jul. 18, 2001.

(30) Foreign Application Priority Data

Jul. 28, 2000 (IT) ..................................... MI2000A1732

(51) Int. Cl.$^7$ .................... A61K 31/728; A61K 31/715; A61K 31/79

(52) U.S. Cl. ...................... 514/54; 536/123.1; 536/119; 424/486; 424/78.36; 424/70.15

(58) Field of Search ........................ 514/54; 536/123.1, 536/119; 424/486, 78.32, 70.14

(56) References Cited

U.S. PATENT DOCUMENTS 4,965,253 A * 10/1990 Goldberg et al.

OTHER PUBLICATIONS

Abatangelo et al., 1983, "Healing of hyaluronic acid–enriched wounds: histological observations," J. Surg. Res.35(5):410–6.
Abatangelo, et al. 1997, "Hyaluronic acid delays or impedes reepithelialization?" J. Burn Care Rehabil. 18(6):552.
Akao, et al., 1992, "Inhibitory Effects of Glycyrrhetic Acid and Its Related Compounds on 3□–Hydroxysteroid Dehydrogenase of Rat Liver Cytosol," Chem. Pharm. Bull. (Tokyo), 40(5):1208–1210.
Allen, L.V. Jr., Contemporary compounding: Products for stomatitis, U. S. Pharmacist 1990;8, pp. 88–90.
Bao, et al., 1997, "Effect of sodium glycyrrhetinate on chemical peritonitis in rats," Chung Kuo Yao Li Hsueh Pao, 18(3): 277–280.
Barker, 1999, "Current practices in the oral management of the patient undergoing chemotherapy or bone marrow transplantation," Support Care Center 7(1):17–20.
Breast Cancer: Changing Diet and Fitness Questions and Answers downloaded from http://my.webmd.com.

Burgess, et al., 1990, "Pharmacological management of recurrent oral mucosal ulceration," Drugs 39(1):54–65.
Cantelli–Forti, et al., 1997, "Toxicological assessment of liquorice: biliary excretion in rats," Pharmacol. Res. 35(5):463–70.
Carrington Oral Wound Rinse for Oral Mucosa http://www.carringtonlabs.com.
Carrington Laboratories/Caraloe Product Ingredients, Radiacare Oral Wound Rinse.
Commentary, 1991, "Oral complications of cancer therapies: diagnosis, prevention, and treatment," The National Institutes of Health Consensus Development Conference Statement, Oncology (Huntingt). 5(7):64, 69–76, 79 passim.
Diary from a Week in Practice dated Dec. 1, 2001, downloaded from www.aafp.org.
Dodd et al., 1996, "Comparison of methods to determine the prevalence and nature of oral mucositis," Cancer Pract. 4(6):312–8.
Dodd, 2001, "A comparison of the affective state and quality of life of chemotherapy patients who do and do not develop chemotherapy–induced oral mucositis," J. Pain Symptom Manage. 21(6):498–505.
Dodds, et al., 1997, "Cortisol metabolism and its inhibition by glycyrrhetinic acid in the isolated perfused human placental lobule," J. Steroid Biochem. Mol. Biol. 62(4):337–43.
Eilers et al., 1988, "Development, testing, and application of the oral assessment guide," Oncol. Nurs. Forum. 15(3):325–30.
Fain Gel: For Vaginal Mucosa http://www.elder–group.com/faingel.html.
Ferrari et al., 2001, "In vivo 11beta–HSD–2 activity: variability, salt–sensitivity, and effect of licorice," Hypertension 38(6):1330–6.
Fujisawa, et al., 2000, "Glycyrrhizin inhibits the lytic pathway of complement—possible mechanism of its anti–inflammatory effect on liver cells in viral hepatitis," Microbiol. Immunol. 44(9):799–804.
Fujiwara, et al., 1983, "Hypokalemia and Sodium Retention in Patients with Diabetes and Chronic Hepatitis Receiving Insulin and Glycyrrhizin," Endocrinol. Japan 20(2):243–249.
Glick, et al., 1992, "Alternative therapies for major aphthous ulcers in AIDS patients," J. Am. Dent. Assoc. 123(7):61–5.
Gupta et al., 1994, "Interpolymer Complexation and its Effect on Bioadhesive Strength and Dissolution Characteristics of Buccal Drug Delivery Systems," Drug Development and Industrial Pharmacy, 20(3):315–325.

(List continued on next page.)

Primary Examiner—Samuel Barts
Assistant Examiner—Michael C. Henry
(74) Attorney, Agent, or Firm—Jones Day

(57) ABSTRACT

The present invention relates to compounds containing as active ingredients hyaluronic acid and polyvinylpyrrolidone, for the treatment of inflammatory, ulcerative and painful conditions of moist epithelial surfaces such as mucositis, stomatitis, vestibulitis, aphthous ulcerations, and Behcet's syndrome.

88 Claims, No Drawings

OTHER PUBLICATIONS

Hanson, et al. 1997, "Protection from radiation–induced oral mucositis by a mouth rinse containing the prostaglandin E1 analog, misoprostol: a placebo–controlled, double–blind clinical trial," Advances in Experimental Medicine & Biology 400B:811–818.

Heilmann, et al., 1999, "Administration of glycyrrhetinic acid: significant correlation between serum levels and the cortisol/cortisone–ratio in serum and urine," Exp. Clin. Endocrinol. Diabetes 107(6):370–8.

Hodgkin's Disease: Chemo downloaded from www.prism.gatech.edu.

Inoue, et al., 1996, "Inhibitory effect of glycyrrhetinic acid derivatives on capsaicin–induced ear edema in mice," Jpn. J. Pharmacol. 71(4):281–9.

Jones, et al., 1998, "Viscoelastic properties of bioadhesive, chlorhexidine–containing semi–solids for topical application to the oropharynx," Pharm. Res. 15(7):1131–6.

Jones, 1997, "Textural analysis and flow rheometry of novel, bioadhesive antimicrobial oral gels," Pharm. Res. 14(4):450–7.

Jones, 1996, "Development and mechanical characterization of bioadhesive semi–solid, polymeric systems containing tetracycline for the treatment of periodontal diseases," Pharm. Res. 13(11):1734–8.

Karthaus, et al., 1999, "Prophylaxis and treatment of chemo– and radiotherapy–induced oral mucositis—are there new strategies?" Bone Marrow Transplant. 24(10):1095–108.

Khaksa, et al., 1996, "Anti–inflammatory and anti–nociceptive activity of disodium glycyrrhetinic acid hemiphthalate," Planta Med. 62(4):326–8.

Larson et al., 1998, "The PRO–SELF Mouth Aware program: an effective approach for reducing chemotherapy–induced mucositis," Cancer Nurs. 21(4):263–8.

LeVeque et al., 1992, "Clinical Evaluation of MG209, an Anesthetic, Film–Forming Agent for Relief from Painful Oral Ulcers Associated with Chemotherapy," J. Clin. Onc. 10(12):1964–1968.

Magic Mouthwash downloaded from www.fpnotebook.com.

"Magic Mouthwash Recipes" updated Nov. 11, 1999.* Downloaded from what–me/hepc/magicmw.html.

Mauricio et al., 1997, "Identification of glycyrrhizin as a thrombin inhibitor," Biochem. Biophys. Res. Commun. 235(1):259–63.

McCarthy et al., 1998, "Risk factors associated with mucositis in cancer patients receiving 5–fluorouracil,"Oral Oncol. 34(6):484–90.

McGuire et al., 1993, "Patterns of mucositis and pain in patients receiving preparative chemotherapy and bone marrow transplantation," Oncol. Nurs. Forum. 20(10):1493–502.

"Mouth Sores" dated Jan. 12, 1997 downloaded from deltronix.com.

Mueller, et al., 1995, "Mucositis management practices for hospitalized patients: national survey results," J. Pain Symptom Manage. 10(7):510–20.

Mueller, et al., 1995, "Pharmaceutical aspects of mucositis mouthwash mixtures," Am. J. Health Syst. Pharm. 52(22):2596–7.

Nagao, 1995, "A case of oral lichen planus with chronic hepatitis C successfully treated by glycyrrhizin," Kansenshogaku Zasshi 69(8):940–4.

North Carolina Board of Pharmacy, Frequently Asked Questions for Pharmacists downloaded from www.ncbop.org.

OraMagic: For Oral Mucosa http://www.fda.gov/cdrh/pdf2/k024180.pdf.

Paoletti, J. and McCord, K., Compounding Mouthwashes and Rinses for Oral Ulcerations, International Journal of Pharmaceutical Compounding, Jan./Feb. 1999.

Pico, et al., 1998, "Mucositis: Its Occurrence Consequences, and Treatment in the Oncology Setting," Oncologist 3(6):446–451.

Plasdone® Povidone USP Technical Profile, International Special Typroducts.

Plevova et al., 1999, "Prevention and treatment of chemotherapy– and radiotherapy–induced oral mucositis: a review," Oral Oncol. 35(5):453–70.

Ploeger, et al., 2001, "The pharmacokinetics of glycyrrhizic acid evaluated by physiologically based pharmacokinetic modeling," Drug Metab. Rev. 33(2):125–47.

ProstaPotek: For Rectal Mucosa http://www.chronicprostatitis.com/algonot.html.

Quilitz, 1995, "Modulation of Chemotherapy–Induced Mucositis," Cancer Control 2(5):452–459.

Randomized clinical trial to treat oral mucositis in patients receiving chemotherapy, dated 1998. Downloaded from www.ons.org.

Ryu et al., 1999, "Increased bioavailability of propranolol in rats by retaining thermally gelling liquid suppositories in the rectum," J. Control Release. 59(2):163–72.

Sanzgiri, et al., 1994, "Evaluation of mucoadhesive properties of hyaluronic acid benzyl esters," International Journal of Pharmaceutics (Netherlands), 107:91–97.

Saxen et al., 1997, "Sustained relief of oral aphthous ulcer pain from topical diclofenac in hyaluronan: a randomized, double–blind clinical trial," Oral Surg. Oral Med. Oral Pathol. Oral Radiol. Endod. 84(4):356–61.

Serra, et al., 2002, "Glycyrrhetinic acid decreases plasma potassium concentrations in patients with anuria," J. Am. Soc. Nephrol. 13(1):191–6.

Shibata, 2000, "A drug over the millennia: pharmacognosy, chemistry, and pharmacology of licorice," Yakugaku Zasshi. 120(10):849–62.

Shintani, et al., 1992, "Glycyrrhizin (Licorice)–Induced Hypokalemic Myopathy," Eur. Neurol. 32:44–51.

Sigurjonsdottir, 2001, "Liquorice–induced rise in blood pressure: a linear dose–response relationship," J. Hum. Hypertens. 15(8):549–52.

Solomonidou, et al., 2001, "Effect of carbomer concentration and degree of neutralization on the mucoadhesive properties of polymer films," J. Biomater. Sci. Polym. Ed. 12(11):1191–205.

Stiff, P., 2001, "Mucositis associated with stem cell transplantation: current status and innovative approaches to management," Bone Marrow Transplant. 27 Suppl 2:S3–S11.

Tips for Giving Medicine That is Hard to Give (Copyright dates from 1997–2000).

Van Rossum, et al., 2001, "'Pseudo–aldosteronism' induced by intravenous glycyrrhizin treatment of chronic hepatitis C patients," Journal of Gastroenterology and Hepatology 16(7):789–795.

Walgreens Kaopectate Children's Anti–diarrheal Liquid Cherry flavor Product Description dowloaded from www.walgreens.com.

Walgreens Kaopectate Concentrated Anti–Diarrheal Peppermint Flavor Product Description dowloaded from www.walgreens.com.

Walgreens Kaopectate Concentrated Anti–diarrheal regular flavor Product Description dowloaded from www.walgreens.com.

Walgreens Maalox Antacid Product Description dowloaded from www.walgreens.com.

Walker, et al., 1995, "Endogenous inhibitors of 11 beta–hydroxysteroid dehydrogenase in hypertension," J. Clin. Endocrinol. Metab. 80(2):529–33.

Walker, et al., 1994, "Licorice–induced hypertension and syndromes of apparent mineralocorticol excess," Endocrinol. Metab. Clin. North Am. 23(2):359–77.

Wang, et al., 2001, "Licorice and cancer," Nutr. Cancer. 39(1):1–11.

Wilkes, 1998, "Prevention and treatment of oral mucositis following cancer chemotherapy," Semin. Oncol. 25(5):538–51.

Wojtaszek, C., 2000, "Management of chemotherapy–induced stomatitis," Clin. J. Oncol. Nurs. 4(6):263–70.

Woo, et al., 1996, "Recurrent aphthous ulcers: a review of diagnosis and treatment," J. Am. Dent. Assoc. 127(8):1202–13.

Yamamura, et al., 1995, "The Relationship Between Pharmacokinetic Behaviour of Glycyrrhizin and Hepatic Function in Patients with Acute Hepatitis and Liver Cirrhosis," Biopharmaceutics and Drug Disposition 15:13–21.

Yamamura, et al., 1992, "Pharmacokinetic profile of glycyrrhizin in healthy volunteers by a new high–performance liquid chromatographic method," J. Pharm. Sci. 81(10):1042–6.

* cited by examiner

COMPOSITIONS AND METHODS FOR THE TREATMENT OR PREVENTION OF INFLAMMATION

The present application is a continuation-in-part of U.S. patent application Ser. No. 10/080,624, filed on Feb. 21, 2002, now abandoned which is a continuation in-part of International Patent Application No. PCT/EP01/08303 filed Jul. 18, 2001, (published as WO 02/09637 in English on Feb. 7, 2002), which in turn claims priority benefits of Italian Patent Application No. MI 2000 A 001732, filed Jul. 28, 2000, the disclosures of each of which are incorporated herein by reference in their entirety.

FIELD OF THE INVENTION

This invention relates to certain compositions useful for the management of painful ulcerative and inflammatory conditions of moist surfaces including the mouth, oropharynx, oesophagus, vagina and rectum (including, but not limited to, mucositis, stomatitis, aphthous ulcerations, and Behcet's syndrome).

BACKGROUND OF THE INVENTION

Aggressive cancer treatment may have toxic effects on normal cells as well as cancer cells. The gastrointestinal tract, including the mouth, is especially affected because these cells are replaced by the body continuously.

Mucositis, an inflammation of the mucous membranes in the mouth, is one of the most common oral problems occurring after chemotherapy and radiation therapy. Mucositis can contribute to oral infections, inability to taste normally and pain arising from the resulting open sores that can develop. Mucositis can become so painful that the patient will not eat or drink, contributing to dehydration and malnutrition.

Radiation therapy to the head and neck for cancers in those areas commonly injure saliva glands and the inside of the mouth which can cause dry mouth, leading to dental disease.

The mucositis problem is not restricted to cancer patients, as mucositis frequently also occurs in HIV patients, particularly when associated with Kaposi's sarcoma, in patients affected with non-Hodgkin's lymphoma, in debilitated elderly patients and in patients receiving BRM treatments like interleukin-2, TNF, interferons, lymphokine-activated lymphocytes and the like.

Such oral problems may make it difficult for the cancer or AIDS patient to receive a complete dose of chemotherapy or radiation therapy. Sometimes treatment must be stopped completely. Such problems are not infrequent: about half of the patients have severe oral lesions that require medical intervention, mostly involving the changes in cancer medication or treatment mentioned above.

Current therapies for mucositis are limited. Cleaning the mouth is recommended to retard the progression of the condition.

Oral cleaning care includes gently cleaning the mouth, moisturizing the lips and mouth, and relieving pain and swelling. A soft toothbrush or toothette cleans teeth well and gently. Cleansing agents can include "salt and soda" (½ tsp. salt and 2 Tbs. of sodium bicarbonate in 32 oz. of warm water), normal saline, sterile water, or sodium bicarbonate (1 tsp. in 8 oz of water). Hydrogen peroxide diluted in equal amounts of water or weak salt water can be used when crusting is present. (This should be used for 1 or 2 days only because it will keep mucositis from healing.) Gentle wiping with a wet gauze dipped in salt water helps remove particles. Toothettes may be too rough for some areas. Particles should be removed before ointments or other medications are put onto the gums or tissues. Rinsing often cleans and moistens the tissues, prevents crusting, and soothes sore gums and tissues. Frequent rinsing prevents particles and bacteria from collecting in the mouth. A salt and baking soda solution neutralizes acids and dissolves thick saliva.

Capsaicin, the active ingredient in hot peppers, reportedly has used to increase a person's ability to tolerate pain. When capsaicin is put on inflamed tissues in the mouth, mucositis pain may decrease as the burning feeling from the capsaicin decreases. Capsaicin is only being used experimentally; however, all side effects are not known.

Mostly, physicians have resorted ice chips or to rather makeshift mixtures of benzocaine with kaopectate and the like. These approaches provide rather limited, temporary relief.

Carrington Laboratories of Irving, Tex. has sold a mucositis product called "Radiacare" for a number of years. However, this product has made limited inroads into the marketplace, and thus has provided few patients relief from the symptoms of mucositis.

Many women get oral aphthous ulceration at specific times of the menstrual cycle and simultaneously get the same kind of ulcers in the genital tract, in particular the vulva and vagina. This is sometimes very severe and can cause retention of urine and require strong painkillers and sedatives. The most severe form is called Behcet's syndrome.

The terms mucositis and stomatitis are often used interchangeably but may include some general distinctions. Mucositis describes a toxic inflammatory reaction affecting the gastrointestinal tract, which may result from exposure to chemotherapeutic agents or ionising radiation. Mucositis typically manifests as an erythematous, burn-like lesion or as random, focal-to-diffuse, ulcerative lesions. Stomatitis refers to an inflammatory reaction affecting the oral mucosa, with or without ulceration, that may be caused or intensified by pharmacological, particularly chemotherapeutic treatments, or by radiotherapy. Stomatitis can range from mild to severe; the patient with severe stomatitis is unable to take anything by mouth.

Thus, there is a clear need for compositions and methods useful for treating or preventing inflammation, including but not limited to, mucositis, stomatitis, aphthous ulcerations, Behcet's syndrome, etc.

Citation of a reference in this or any section of the specification shall not be construed as an admission that such reference is prior art to the present invention.

SUMMARY OF THE INVENTION

The present invention is directed to a composition comprising from about 0.01 to about 5 percent by weight of hyaluronic acid, or a pharmaceutically acceptable salt thereof, having a molecular weight from about 1.6 and 2.2 million daltons; from about 0.04 to about 15% by weight of a K60 to K100 polyvinylpyrrolidone; and from about 86 to about 98% water. In one embodiment, the viscosity of the composition is from about 50 to about 500 centipoise. In an embodiment the polyvinylpyrrolidone is from about K85 to about K95 and is from about 3 to about 10% by weight of the composition. In another embodiment, the polyvinylpyrrolidone is from about 7 to about 10% by weight of the composition. In yet another embodiment, the hyaluronic acid, or the pharmaceutically acceptable salt thereof, is from about 1.8 to about 2.0 million daltons, and from about 0.01 to about 2% by weight of the composition, and wherein the viscosity of the composition is from about 90 to about 1000 centipoise. In yet another embodiment, the hyaluronic acid, or the pharmaceutically acceptable salt thereof, is from about 1.8 to about 2.0 million daltons and from about 0.01% to about 2% by weight of the composition. In an embodiment, the viscosity of the composition is from about 90 to about 1000 centipoise. In a preferred embodiment, the composition is in the form of a gel.

The present invention is also directed to a composition comprising from about 0.04 to about 5 percent by weight of hyaluronic acid, or a pharmaceutically acceptable salt thereof, with a molecular weight from about 1.6 to about 2.2 million daltons; from about 0.08 to about 15% by weight of a K60 to K100 polyvinylpyrrolidone; and from about 86 to about 98% water. In one embodiment, the viscosity of the composition is from about 50 to about 500 centipoise. In an embodiment, the polyvinylpyrrolidone, is from about K85 to about K95, and is from about 6 to about 12% by weight of the composition. In another embodiment, the polyvinylpyrrolidone is from about 8 to about 10% by weight of the composition. In yet another embodiment, the hyaluronic acid, or the pharmaceutically acceptable salt thereof, is from about 1.8 to about 2.0 million daltons and from about 0.04 to about 2% by weight of the composition. In yet another embodiment, the hyaluronic acid, or the pharmaceutically acceptable salt thereof is from about 1.8 to about 2.0 million daltons and from about 0.04 to about 2% by weight of the composition. In a preferred embodiment, the composition is in the form of a gel.

The present invention is also directed to a flexible packet comprising a composition comprising from about 0.04 to about 5 percent by weight of hyaluronic acid, or a pharmaceutically acceptable salt thereof, with a molecular weight from about 1.6 to about 2.2 million daltons; from about 0.08 to about 15% by weight of a K60 to K100 polyvinylpyrrolidone; and from about 86 to about 98% water. In one embodiment, the viscosity of the composition is from about 50 to about 500 centipoise. In a preferred embodiment, the packet is a sealed pouch comprising from about 10 to about 30 milliliters of the composition. The present invention is also directed to a flexible packet comprising a composition comprising hyaluronic acid, or a pharmaceutically acceptable salt thereof, glycyrrhetinic acid, or a pharmaceutically acceptable salt thereof, and polyvinylpyrrolidone.

The present invention is also directed to a composition comprising hyaluronic acid, or a pharmaceutically acceptable salt thereof, glycyrrhetinic acid, or a pharmaceutically acceptable salt thereof, and polyvinylpyrrolidone. In an embodiment, the composition further comprises a viscosity-increasing agent, surfactant, stabilizing agent/preservative, flavor, fragrance, sweetening agent, bioadhesive agent, or a co-solubilizer. The composition may also further comprise a cellulose derivative, acrylic or methacrylic acid polymer or copolymer, ethylene or propylene glycol, polyethoxylated hydrogenated castor oil, EDTA, sodium benzoate, sodium or potassium sorbate, dextrin, sodium saccharin, or aspartame. In yet another embodiment, the composition further comprises an antibacterial agent, disinfectant agent, antifungal agent, analgesic, anti-inflammatory, emollient, or a local anesthetic.

The present invention is also directed to a method for treating or preventing inflammation in a patient comprising administering to a patient in need thereof an effective amount of a composition comprising from about 0.01 to about 5 percent by weight of hyaluronic acid, or a pharmaceutically acceptable salt thereof, having a molecular weight from about 1.6 to about 2.2 million daltons; from about 0.04 to about 15% by weight of a K60 to K100 polyvinylpyrrolidone; and from about 86 to about 98% water. In one embodiment, the viscosity of the composition is from about 50 to about 500 centipoise. In an embodiment, the composition is administered at least twice daily for at least two consecutive days. In yet another embodiment, the composition is administered at least three times daily for at least four consecutive days. In yet another embodiment, the composition is administered at least three times daily for at least seven consecutive days.

The present invention is also directed to a method for treating or preventing inflammation in a patient, comprising administering to a patient in need thereof an effective amount of a composition comprising hyaluronic acid, or a pharmaceutically acceptable salt thereof, glycyrrhetinic acid, or a pharmaceutically acceptable salt thereof, and polyvinylpyrrolidone. In an embodiment, the composition is administered at least twice daily for at least two consecutive days. In yet another embodiment, the composition is administered at least three times daily for at least four consecutive days. In yet another embodiment, the composition is administered at least three times daily for at least seven consecutive days. In addition to its ordinary meaning, the term treatment encompasses inhibition of progression of symptoms or amelioration of symptoms of inflammation and mucositis.

The present invention is also directed to a method for treating or preventing inflammation in the oral cavity of a patient comprising having a patient in need thereof gargle an effective amount of a composition comprising from about 0.01 to about 5 percent by weight of hyaluronic acid, or a pharmaceutically acceptable salt thereof, having a molecular weight from about 1.6 to about 2.2 million daltons; from about 0.04 to about 15% by weight of a K60 to K100 polyvinylpyrrolidone; and from about 86 to about 98% water. In one embodiment, the viscosity of the composition is from about 50 to about 500 centipoise. The present invention is also directed to a method for treating or preventing inflammation in the oral cavity of a patient comprising having a patient in need thereof gargle an effective amount of a composition comprising hyaluronic acid or a pharmaceutically acceptable salt thereof; glycyrrhetinic acid or a pharmaceutically acceptable salt thereof; and polyvinylpyrrolidone.

The present invention is directed to a method for treating or preventing mucositis in a patient comprising administering to a patient in need thereof an effective amount of a composition comprising from about 0.01 to about 5 percent by weight of hyaluronic acid, or a pharmaceutically acceptable salt thereof, having a molecular weight from about 1.6 to about 2.2 million daltons; from about 0.04 to about 15% by weight of a K60 to K100 polyvinylpyrrolidone; and from about 86 to about 98% water. In one embodiment, the viscosity of the composition is from about 50 to about 500 centipoise. The present invention is also directed to a method for treating or preventing mucositis in a patient comprising administering to a patient in need thereof an effective amount of a composition comprising hyaluronic acid or a pharmaceutically acceptable salt thereof; glycyrrhetinic acid or a pharmaceutically acceptable salt thereof; and polyvinylpyrrolidone.

The present invention is directed to a method for treating pain resulting from oral surgery in a patient in need thereof comprising having a patient in need thereof gargle an effective amount of a composition comprising from about 0.01 to about 5 percent by weight of hyaluronic acid, or a pharmaceutically acceptable salt thereof, having a molecular weight from about 1.6 to about 2.2 million daltons; from about 0.04 to about 15% by weight of a K60 to K100 polyvinylpyrrolidone; and from about 86 to about 98% water. In one embodiment, the viscosity of the composition is from about 50 to about 500 centipoise. The present invention is also directed to a method for treating pain resulting from oral surgery in a patient in need thereof comprising having a patient in need thereof gargle an effective amount of a composition comprising hyaluronic acid or a pharmaceutically acceptable salt thereof; glycyrrhetinic acid or a pharmaceutically acceptable salt thereof; and polyvinylpyrrolidone.

The present invention can be more fully explained by reference to the following detailed description and illustrative examples.

DETAILED DESCRIPTION OF THE INVENTION

Surprisingly, the topical administration of a formulation comprising an effective amount of hyaluronic acid, or a pharmaceutically acceptable salt thereof, and polyvinylpyrrolidone provides an effective therapeutical or preventive treatment for mucositis and stomatitis of various origin and severity and, more generally, of the lesions of the oropharynx cavity and oesophagus, particularly those caused by dental devices and by radio- or chemotherapy and by surgery.

Without being bound by a particular mode of action, the favorable therapeutic results obtained by the use of the compositions of the present invention are believed to be due to both the interactions between hyaluronic acid, or a pharmaceutically acceptable salt thereof, and polyvinylpyrrolidone, and the capability of the formulation of adhering to the oral mucosa providing a protective coating for the exposed nerve endings, and thus, reduction of pain and promoting cicatrisation and healing of the lesions. Furthermore, it is believed that the moisturizing effect of the compositions has beneficial effect as it protects mucous membranes from further irritating lesions.

In one embodiment, the present invention involves a composition comprising from about 0.01 to about 5 percent by weight of hyaluronic acid, or a pharmaceutically acceptable salt thereof, having a molecular weight from about 1.6 to about 2.2 million daltons; from about 0.04 to about 15% by weight of a K60 to K100 polyvinylpyrrolidone; and from about 86 to about 98% water. In one embodiment, the viscosity of the composition is from about 50 to about 500 centipoise.

In an alternative embodiment, the present invention involves a composition comprising from about 0.04 to about 5 percent by weight of hyaluronic acid, or a pharmaceutically acceptable salt thereof, having a molecular weight from about 1.6 to about 2.2 million daltons; from about 0.08 to about 15% by weight of a K60 to K100 polyvinylpyrrolidone; and from about 86 to about 98% water. In one embodiment, the viscosity of the composition is from about 50 to about 500 centipoise. The compositions of the present invention can be diluted with water, and accordingly, is useful for obtaining the above compositions. In an alternative embodiment, the composition can be diluted with physiological saline.

These compositions can be used by themselves or in admixture with one or more medicaments, excipients and/or adjuvants, preferably forming a viscous and lubricating substance that remains adherent to the surface epithelium. These compositions are suitable for topical administration to epithelial surfaces such as, but not limited to, the oropharynx and oesophagus.

A further aspect of the invention concerns the use of hyaluronic acid, or a pharmaceutically acceptable salt thereof, glycyrrhetinic acid, or a pharmaceutically acceptable salt thereof, and polyvinylpyrrolidone for treating or preventing inflammation in a patient. In one embodiment, the inflammation is of epithelial surfaces such as, but not limited to, the oral mucosa, particularly mucositis and stomatitis.

Preferably, the compositions of the present invention are administered by topical application. In a particular embodiment in which the composition is administered to the oral cavity, the patient, after gargling with the composition, and if desired, may refrain from eating or drinking for a certain time, ranging from minutes up to hours after gargling. Alternatively, the patient, if desired, may eat or drink immediately after gargling.

The compositions of the invention are preferably in the form of a slightly viscous aqueous liquid (gel) which provides a film-forming and coating effect on the epithelial surfaces such as, but not limited to, the oral mucosa.

As explained above, the present invention relates to a composition comprising from about 0.01 to about 5 percent by weight of hyaluronic acid, or a pharmaceutically acceptable salt thereof, having a molecular weight from about 1.6 and 2.2 million daltons; from about 0.04 to about 15% by weight of a K60 to K100 polyvinylpyrrolidone; and from about 86 to about 98% water. In one embodiment, the viscosity of the composition is from about 50 to about 500 centipoise. In an embodiment, the polyvinylpyrrolidone is from about K85 and K95 and is from about 3 and 10% by weight of the composition. Most preferably, the polyvinylpyrrolidone is from about 7 to about 10% by weight of the composition. Preferably, the hyaluronic acid, or the pharmaceutically acceptable salt thereof, is from about 1.8 to about 2.0 million daltons and from about 0.01 to about 2% by weight. In one embodiment, the viscosity of the composition is from about 90 to about 1000 centipoise. Preferably, the composition is in the form of a gel. Most preferably, the hyaluronic acid, or the pharmaceutically acceptable salt thereof, is from about 1.8 to about 2.0 million daltons and from about 0.01 to about 2% by weight of the composition, the viscosity of the composition is from about 90 to about 1000 centipoise and the composition is in the form of a gel. Further, glycyrrhetinic acid, or a pharmaceutically acceptable salt thereof, can be present in weight percentages ranging from about 0.01 to about 3% by weight of the composition.

The viscosity of the compositions can be measured using routine methods. In particular, viscosity can be measured using a Brookfield Model DV1+ viscometer (Middleboro, Mass.) at room temperature, preferably at about 22°–25° C., or using a Haake Model VT02 viscometer (Karlsruhe, Germany) at room temperature, preferably at about 22°–25° C.

In a particular embodiment of the present invention, the compositions are provided in a concentrated form for later dilution with water. The compositions comprise from about 0.04 to about 5 percent by weight of hyaluronic acid, or a pharmaceutically acceptable salt thereof, having a molecular weight from about 1.6 to about 2.2 million daltons; from about 0.08 to about 15% by weight of a K60 to K100 polyvinylpyrrolidone; and from about 86 to about 98% water. In one embodiment, the viscosity of the composition is from about 50 to about 500 centipoise. These compositions preferably comprise polyvinylpyrrolidone from about K85 to about K95 and from about 6 to about 12% by weight of the composition, most preferably from about 8 to about 10% by weight of the composition; and comprise hyaluronic acid, or a pharmaceutically acceptable salt thereof, having a molecular weight from about 1.8 to about 2.0 million daltons and from about 0.04 to about 2% by weight of the composition. Preferably, hyaluronic acid, or the pharmaceutically acceptable salt thereof, is from about 1.8 to about 2.0 million daltons in molecular weight and from about 0.04 to about 2% by weight of the composition.

Examples of pharmaceutically acceptable salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound having an acidic functional group, such as a carboxylic acid or sulfonic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butyl amine, or tris-(hydroxymethyl)methylamine, N, N,-di-lower alkyl-N-(hydroxy lower alkyl)-amines, such as N, N,-dimethyl-N-(2-hydroxyethyl)amine, or tri-(2-hydroxyethyl)amine; N-methyl-D-glucamine; and amino acids such as arginine, lysine, and the like.

The compositions of the present inventions can comprise a pharmaceutically acceptable excipient, preferably for topical administration, such as one or more of the following:

viscosity-increasing agent;

surfactant;

stabilizing agent/preservative;

flavor, fragrance, sweetening agent;

bioadhesive;

co-solubilizer.

Examples of said excipients comprise cellulose derivatives, acrylic or methacrylic acids polymers or copolymers, ethylene or propylene glycols, polyethoxylated hydrogenated castor oil, EDTA, sodium benzoate, sodium or potassium sorbate, dextrins, sodium saccharin, aspartame and other excipients conventionally used in the formulation of collutories or liquid oral forms. Oral formulation can include standard carriers such as pharmaceutical grades of mannitol, lactose, starch, magnesium stearate, sodium saccharine, cellulose, magnesium carbonate, etc. Additional examples of suitable excipients are described in "Remington's Pharmaceutical Sciences" by E. W. Martin.

The compositions of the present invention may further comprise one or more other active ingredients, such as an antibacterial, disinfectant, antifungal, analgesic, other anti-inflammatory, emollients, local anaesthetics and the like. Suitable antimicrobials include, but are not limited to, quaternary ammonium salts such as benzalkonium chloride.

The precise dose to be employed in the composition will depend on the route of administration, and the seriousness of the disease or disorder, and should be decided according to the judgment of the practitioner and each patient's circumstances. In principle, however, for oral applications, a wash or gargle with 10–50 ml of solution, optionally diluted in water, for a time of about up to two or three minutes at least two but preferably three times or more daily, most preferably before meals, will be sufficient to provide an optimal therapeutic or preventive response. The treatment can be protracted until remission of symptoms, usually for at least 2 days, but preferably 5–10 days. More prolonged treatments are not contraindicated, considering the low, if any, toxicity of the components of the formulations of the invention.

The present invention also provides a pharmaceutical pack or kit comprising one or more containers, e.g. a flexible packet, vial, ampoule, bottle and the like, filled with one or more of the ingredients of the compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a preferred embodiment, the compositions of the present invention can be presented as single- or multi-dose forms in a flexible packet. Preferably, the compositions of the present invention are packaged in the concentrated form in flexible packets with a dose of from about 10 to about 30 ml per packet that can be diluted with water to create about 40–60 ml of product for use by the patient.

The following series of examples are presented by way of illustration and not by way of limitation on the scope of the invention.

EXAMPLE 1

Qualitative-quantitative composition percent composition:

| Ingredient | % By Weight |
| --- | --- |
| Sodium hyaluronate | 0.1 |
| Glycyrrhetinic acid | 0.06 |
| PVP (K60 to K100) | 9.0 |
| Maltodextrin | 6.00 |
| Propylene glycol | 2.94 |
| Potassium sorbate | 0.3 |
| Sodium benzoate | 0.3 |
| Hydroxyethyl cellulose | 1.5 |
| Hydrogenated castor oil PEG-40 | 0.27 |
| Disodium EDTA | 0.1 |
| Benzalkonium chloride | 0.5 |
| Perfume (Glycyrrhiza Comp. 2717) | 0.16 |
| Sodium saccharin | 0.1 |
| Depurated water | 78.44 |

To prepare this composition, water was placed in a turboemulsifier, then a mixture of potassium sorbate, sodium benzoate and disodium EDTA was added, followed by hyaluronic acid and maltodextrin. The mixture was stirred after each addition until complete dissolution of the components. After that, PVP was slowly added under stirring and vacuum (30 mm Hg) until complete solvation. Then sodium saccharin and hydroxyethylcellulose were subsequently added, the whole was subjected to vacuum and left under stirring until complete solvation. Afterwards, hydrogenated castor oil 40/OE and perfume, benzalkonium chloride, and a mixture of propylene glycol and glycyrrhetinic acid were added in that order, stirring after each addition until complete dissolution of the components. When the additions were completed, the mixture was stirred under vacuum for 30 minutes.

For a concentrated version of the invention, 10 ml or 15 ml of the above composition were distributed in a packet or mono-dose vial, which can be diluted with 30–50 ml of water before use; for the ready-to-use version, the composition disclosed above was diluted with depurated water to a concentration of 50%, and 200 ml or 300 ml of the resulting composition were distributed in bottles.

EXAMPLE 2

In vivo Data

Thirty patients, of age range from 30 to 60 years, were evaluated, 10 of them were AIDS patients 30 to 40 years of age who were also receiving anti-retroviral therapy. All patients in the study were affected with inflammatory pathologies of the oral cavity of various aetiology:

12 cases of oro-pharyngeal mucositis;

4 cases of aphthous lesions of the oral cavity;

4 cases of post-traumatic lesions;

3 cases of Lichen Planus of the oral cavity;

3 cases of radiotherapy-induced stomatitis;

3 cases of oral cavity surgery side effects; and 1 case of leukoplakia.

Patients were treated with the composition described in Example 1 in 15 ml sachets (packets) diluted in water in a 1:4 ratio. The slightly viscous solution was retained in the mouth for 2–3 minutes during which it was gargled and swirled about to obtain homogeneous distribution on the whole surface of the oral mucosa. The solution was then discharged. The patients refrained from eating or drinking for various times after gargling ranging from immediately after gargling to more than 1 hour after gargling.

The formulation was used three times a day 60 minutes before meal times for seven consecutive days.

At the end of the treatment, the extent of inflammation and lesions, the decrease or disappearance of dysphagia for solid and semi-solid foods, and liquids, and the duration of the activity of the product were evaluated.

After the first administration, more than 80% of patients perceived within a few hours reduction of pain so as to permit food intake. The effect lasted three or four hours.

Healing of the lesions of the oral mucosa occurred after 3–4 days of treatment in about 60% of treated cases. The percentage reached 90% at the end of one week of treatment. In the remaining three cases only a pathological condition persisted, but with improved symptoms compared with the beginning of the treatment, providing a remarkable improvement of life quality and restoring a normal, differentiated diet.

EXAMPLE 3

Two patients with throat pain (sore throat) were unable to obtain relief with analgesics or other topical agents. Patients were treated with the composition described in Example 1 in 15 ml packets, the contents of which were diluted in water in a 1:4 ratio. The solution was retained in the mouth for about one minute during which time it was gargled to obtain good contact with the tissues of the throat. The solution was then discharged. Within ten minutes, the patients experienced dramatic relief of their sore throat symptoms, which relief persisted for several hours.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A composition, comprising:
   from about 0.01 to about 5 percent by weight of hyaluronic acid, or a pharmaceutically acceptable salt thereof, having a molecular weight from about 1.6 to about 2.2 million daltons;
   from about 0.04 to about 15% by weight of a K60 to K100 polyvinylpyrrolidone; and
   from about 86 to about 98% water,
   wherein the viscosity of the composition is from about 50 to about 500 centipoise.

2. The composition of claim 1, wherein the polyvinylpyrrolidone is from about K85 to about K95 and is from about 3 to about 10% by weight of the composition.

3. The composition of claim 2, wherein the polyvinylpyrrolidone is from about 7 to about 10% by weight of the composition.

4. A composition, comprising:
   from about 0.01 to about 2 percent by weight of hyaluronic acid, or a pharmaceutically acceptable salt thereof, having a molecular weight from about 1.8 to about 2.0 million daltons,
   from about 0.04 to about 15% by weight of a K60 to K100 polyvinylpyrrolidone; and
   from about 86 to about 98% water,
   wherein the viscosity of the composition is from about 90 to about 1000 centipoise.

5. The composition of claim 4, in the form of a gel.

6. The composition, comprising:
   from about 0.01 to about 2 percent by weight of hyaluronic acid, or a pharmaceutically acceptable salt thereof, having a molecular weight from about 1.8 to about 2.0 million daltons,
   from about 7 to about 10% by weight of a K60 to K100 polyvinylpyrrolidone; and
   from about 86 to about 98% water,
   wherein the viscosity of the composition is from about 90 to about 1000 centipoise.

7. The composition of claim 6, in the form of a gel.

8. The composition of claim 1, further comprising a viscosity-increasing agent, surfactant, stabilizing agent/preservative, flavour, fragrance, sweetening agent, bioadhesive agent, or a co-solubilizer.

9. The composition of claim 8, further comprising a cellulose derivative, acrylic or methacrylic acid polymer or copolymer, ethylene or propylene glycol, polyethoxylated hydrogenated castor oil, EDTA, sodium benzoate, sodium or potassium sorbate, dextrin, sodium saccharin, or aspartame.

10. The composition of claim 1, further comprising an antibacterial agent, disinfectant agent, antifungal agent, analgesic, anti-inflammatory, emollient, or a local anesthetic.

11. The composition of claim 1, further comprising glycyrrhetinic acid or a pharmaceutically acceptable salt thereof.

12. A composition comprising:
from about 0.04 to about 5 percent by weight of hyaluronic acid, or a pharmaceutically acceptable salt thereof, with a molecular weight from about 1.6 to about 2.2 million daltons;
from about 0.08 to about 15% by weight of a K60 to K100 polyvinylpyrrolidone; and
from about 86 to about 98% water,
wherein the viscosity of the composition is from about 50 to about 500 centipoise.

13. The composition of claim 12, wherein the polyvinylpyrrolidone is from about K85 to about K95, and is from about 6 to about 12% by weight of the composition.

14. The composition of claim 13, wherein the polyvinylpyrrolidone is from about 8 to about 10% by weight of the composition.

15. The composition of claim 12, wherein the hyaluronic acid, or the pharmaceutically acceptable salt thereof, is from about 1.8 to about 2.0 million daltons and from about 0.04 to about 2% by weight of the composition.

16. The composition of claim 15, in the form of a gel.

17. The composition of claim 14, wherein the hyaluronic acid, or the pharmaceutically acceptable salt thereof, is from about 1.8 to about 2.0 million daltons and from about 0.04 to about 2% by weight of the composition.

18. The composition of claim 17, in the form of a gel.

19. The composition of claim 12, further comprising a viscosity-increasing agent, surfactant, stabilizing agent/preservative, flavour, fragrance, sweetening agent, bioadhesive agent, or a co-solubilizer.

20. The composition of claim 19, further comprising a cellulose derivative, acrylic or methacrylic acid polymer or copolymer, ethylene or propylene glycol, polyethoxylated hydrogenated castor oil, EDTA, sodium benzoate, sodium or potassium sorbate, dextrin, sodium saccharin, or aspartame.

21. The composition of claim 12, further comprising an antibacterial agent, disinfectant agent, antifungal agent, analgesic, anti-inflammatory, emollient, or a local anesthetic.

22. The composition of claim 12, further comprising glycyrrhetinic acid or a pharmaceutically acceptable salt thereof.

23. A flexible packet comprising the composition of claim 12.

24. The packet of claim 23, being a sealed pouch comprising from about 10 to about 30 milliliters of the composition.

25. A composition comprising hyaluronic acid or a pharmaceutically acceptable salt thereof; glycyrrhetinic acid or a pharmaceutically acceptable salt thereof; and polyvinylpyrrolidone.

26. A flexible packet comprising the composition of claim 25.

27. The composition of claim 25, further comprising a viscosity-increasing agent, surfactant, stabilizing agent/preservative, flavour, fragrance, sweetening agent, bioadhesive agent, or a co-solubilizer.

28. The composition of claim 27, further comprising a cellulose derivative, acrylic or methacrylic acid polymer or copolymer, ethylene or propylene glycol, polyethoxylated hydrogenated castor oil, EDTA, sodium benzoate, sodium or potassium sorbate, dextrin, sodium saccharin, or aspartame.

29. The composition of claim 25, further comprising an antibacterial agent, disinfectant agent, antifungal agent, analgesic, anti-inflammatory, emollient, or a local anesthetic.

30. A method for treating or preventing inflammation in a patient comprising:

administering to a patient in need thereof an effective amount of a composition comprising:
(i) from about 0.01 to about 5 percent by weight of hyaluronic acid, or a pharmaceutically acceptable salt thereof, having a molecular weight from about 1.6 to about 2.2 million daltons;
(ii) from about 0.04 to about 15% by weight of a K60 to K100 polyvinylpyrrolidone; and
(iii) from about 86 to about 98% water,
wherein the viscosity of the composition is from about 50 to about 500 centipoise.

31. The method of claim 30, wherein the composition is administered at least twice daily for at least two consecutive days.

32. The method of claim 30, wherein the composition is administered at least three times daily for at least four consecutive days.

33. The method of claim 30, wherein the composition is administered at least three times daily for at least seven consecutive days.

34. The method of claim 30, wherein the composition further comprises a viscosity-increasing agent, surfactant, stabilizing agent/preservative, flavour, fragrance, sweetening agent, bioadhesive agent, or a co-solubilizer.

35. The method of claim 34, wherein the composition further comprises a cellulose derivative, acrylic or methacrylic acid polymer or copolymer, ethylene or propylene glycol, polyethoxylated hydrogenated castor oil, EDTA, sodium benzoate, sodium or potassium sorbate, dextrin, sodium saccharin, or aspartame.

36. The method of claim 30, wherein the composition further comprises an antibacterial agent, disinfectant agent, antifungal agent, analgesic, anti-inflammatory, emollient, or a local anesthetic.

37. The method of claim 30, wherein the administration is by topical application.

38. The method of claim 30, wherein the composition further comprises glycyrrhetinic acid or a pharmaceutically acceptable salt thereof.

39. A method for treating or preventing inflammation in a patient, comprising administering to a patient in need thereof an effective amount of a composition comprising hyaluronic acid or a pharmaceutically acceptable salt thereof; glycyrrhetinic acid or a pharmaceutically acceptable salt thereof; and polyvinylpyrrolidone.

40. The method of claim 39, wherein the administration is by topical application.

41. The method of claim 39, wherein the composition is administered at least twice daily for at least two consecutive days.

42. The method of claim 39, wherein the composition is administered at least three times daily for at least four consecutive days.

43. The method of claim 39, wherein the composition is administered at least three times daily for at least seven consecutive days.

44. The method of claim 39, wherein the composition further comprises a viscosity-increasing agent, surfactant, stabilizing agent/preservative, flavour, fragrance, sweetening agent, bioadhesive agent, or a co-solubilizer.

45. The method of claim 44, wherein the composition further comprises a cellulose derivative, acrylic or methacrylic acid polymer or copolymer, ethylene or propylene glycol, polyethoxylated hydrogenated castor oil, EDTA, sodium benzoate, sodium or potassium sorbate, dextrin, sodium saccharin, or aspartame.

46. The method of claim 39, wherein the composition further comprises an antibacterial agent, disinfectant agent, antifungal agent, analgesic, anti-inflammatory, emollient, or a local anesthetic.

47. A method for treating or preventing inflammation in the oral cavity of a patient comprising:
   administering to the oral cavity of a patient in need thereof an effective amount of a composition comprising:
   (i) from about 0.01 to about 5 percent by weight of hyaluronic acid, or a pharmaceutically acceptable salt thereof, having a molecular weight from about 1.6 to about 2.2 million daltons;
   (ii) from about 0.04 to about 15% by weight of a K60 to K100 polyvinylpyrrolidone; and
   (iii) from about 86 to about 98% water,
   wherein the viscosity of the composition is from about 50 to about 500 centipoise.

48. A method for treating or preventing inflammation in the oral cavity of a patient comprising:
   administering to the oral cavity of a patient in need thereof an effective amount of a composition comprising hyaluronic acid or a pharmaceutically acceptable salt thereof; glycyrrhetinic acid or a pharmaceutically acceptable salt thereof; and polyvinylpyrrolidone.

49. The method of claim 47, wherein the composition further comprises glycyrrhetinic acid or a pharmaceutically acceptable salt thereof.

50. A method for treating or preventing mucositis in a patient comprising:
   administering to a patient in need thereof an effective amount of a composition comprising:
   (i) from about 0.01 to about 5 percent by weight of hyaluronic acid, or a pharmaceutically acceptable salt thereof, having a molecular weight from about 1.6 to about 2.2 million daltons;
   (ii) from about 0.04 to about 15% by weight of a K60 to K100 polyvinylpyrrolidone; and
   (iii) from about 86 to about 98% water,
   wherein the viscosity of the composition is from about 50 to about 500 centipoise.

51. A method for treating or preventing mucositis in a patient comprising:
   administering to a patient in need thereof an effective amount of a composition comprising hyaluronic acid or a pharmaceutically acceptable salt thereof; glycyrrhetinic acid or a pharmaceutically acceptable salt thereof; and polyvinylpyrrolidone.

52. The method of claim 50 or 51, wherein the composition is administered at least twice daily for at least two consecutive days.

53. The method of claim 50 or 51, wherein the composition is administered at least three times daily for at least four consecutive days.

54. The method of claim 50 or 51, wherein the composition is administered at least three times daily for at least seven consecutive days.

55. The method of claim 50, wherein the composition further comprises glycyrrhetinic acid or a pharmaceutically acceptable salt thereof.

56. A method for treating pain resulting from oral surgery in a patient in need thereof comprising:
   having a patient in need thereof gargle an effective amount of a composition comprising:
   (i) from about 0.01 to about 5 percent by weight of hyaluronic acid, or a pharmaceutically acceptable salt thereof, having a molecular weight from about 1.6 to about 2.2 million daltons;
   (ii) from about 0.04 to about 15% by weight of a K60 to K100 polyvinylpyrrolidone; and
   (iii) from about 86 to about 98% water,
   wherein the viscosity of the composition is from about 50 to about 500 centipoise.

57. A method for treating pain resulting from oral surgery in a patient in need thereof comprising:
   having a patient in need thereof gargle an effective amount of a composition comprising hyaluronic acid or a pharmaceutically acceptable salt thereof; glycyrrhetinic acid or a pharmaceutically acceptable salt thereof, and polyvinylpyrrolidone.

58. The method of claim 56 or 57, wherein the patient gargles the composition at least twice daily for at least two consecutive days.

59. The method of claim 56 or 57, wherein the patient gargles the composition at least three times daily for at least four consecutive days.

60. The method of claim 56 or 57, wherein the patient gargles the composition at least three times daily for at least seven consecutive days.

61. The method of claim 56, wherein the composition further comprises glycyrrhetinic acid or a pharmaceutically acceptable salt thereof.

62. A composition, comprising about 0.1% by weight sodium hyaluronate, about 0.06% by weight glycyrrhetinic acid, about 9.0% by weight PVP (K60 to K100), about 6.0% by weight maltodextrin, about 2.94% by weight propylene glycol, about 0.3% by weight potassium sorbate, about 0.3% by weight sodium benzoate, about 1.5% by weight hydroxyethyl cellulose, about 0.27% by weight hydrogenated castor oil PEG-40, about 0.1% by weight disodium EDTA, about 0.5% by weight benzalkonium chloride, about 0.16% by weight perfume, about 0.1% by weight sodium saccharin, and about 78.44% by weight water.

63. A method for treating or preventing inflammation in a patient comprising administering to a patient in need thereof an effective amount of the composition of claim 62.

64. A method for treating or preventing inflammation in the oral cavity of a patient comprising administering to the oral cavity of a patient in need thereof an effective amount of the composition of claim 62.

65. A method for treating or preventing mucositis in a patient comprising administering to a patient in need thereof an effective amount of the composition of claim 62.

66. A method for treating pain resulting from oral surgery in a patient in need thereof comprising having a patient in need thereof gargle an effective amount of the composition of claim 62.

67. The composition of claim 1, 4, 6 or 12, wherein the viscosity is measured using a Brookfield Model DV1+ viscometer at 22°–25° C., or using a Haake Model VT02 viscometer at 22°–25° C.

68. The method of claim 30, 47, 50 or 56, wherein the viscosity is measured using a Brookfield Model DV1+ viscometer at 22°–25° C., or using a Haake Model VT02 viscometer at 22°–25° C.

69. The method of claim 30, 39 or 63, wherein the inflammation is mucositis, stomatitis or an aphthous ulcer.

70. The method of claim 30, 39 or 63, wherein the inflammation occurs in the oral cavity.

71. The method of claim 30, 39 or 63, wherein the inflammation occurs in the oro-pharynx.

72. The method of claim 30, 39 or 63, wherein the inflammation occurs in the oesophagus.

73. The method of claim 30, 39 or 63, wherein the inflammation occurs in the vagina.

74. The method of claim 30, 39 or 63, wherein the inflammation occurs in the rectum.

75. The method of claim 30, 39 or 63, wherein the patient has Behcet's syndrome.

76. The method of claim 47, 48 or 64, wherein the inflammation is mucositis, stomatitis or an aphthous ulcer.

77. The method of claim 47, 48 or 64, wherein administering comprises gargling the composition.

78. The method of claim 47, 48 or 64, wherein the inflammation is caused by a post-traumatic lesion, lichen planus, radiotherapy-induced stomatitis or leukoplakia.

79. The method of claim 50, 51 or 65, wherein the mucositis occurs in the oral cavity.

80. The method of claim 50, 51 or 65, wherein the mucositis occurs in the oro-pharynx.

81. The method of claim 50, 51 or 65, wherein the mucositis occurs in the oesophagus.

82. The method of claim 50, 51 or 65, wherein the mucositis occurs in the vagina.

83. The method of claim 50, 51 or 65, wherein the mucositis occurs in the rectum.

84. The method of claim 50, 51 or 65, wherein the patient has Behcet's syndrome.

85. The method of claim 77, wherein the patient gargles the composition at least twice daily for at least two consecutive days.

86. The method of claim 77, wherein the patient gargles the composition at least three times daily for at least four consecutive days.

87. The method of claim 77, wherein the patient gargles the composition at least three times daily for at least seven consecutive days.

88. The method of claim 77, wherein the patient avoids eating or drinking for at least one hour after gargling.

* * * * *